United States Patent [19]

Yamashita et al.

[11] Patent Number: 4,764,117
[45] Date of Patent: Aug. 16, 1988

[54] RESTORATIVE DENTAL MATERIAL AND METHOD OF RESTORING TEETH USING SAME

[75] Inventors: Atsushi Yamashita; Toshiaki Yamami; Yasuhiro Kondo; Hiroyuki Nakai; Kazuomi Suzuki, all of Okayama, Japan

[73] Assignee: Kuraray Co., Ltd., Kurashiki, Japan

[21] Appl. No.: 948,360

[22] PCT Filed: Jan. 24, 1986

[86] PCT No.: PCT/JP86/00030
§ 371 Date: Nov. 24, 1986
§ 102(e) Date: Nov. 24, 1986

[87] PCT Pub. No.: WO86/05677
PCT Pub. Date: Oct. 9, 1986

[30] Foreign Application Priority Data

Apr. 3, 1985 [JP] Japan ............................ 60-71477
Sep. 30, 1985 [JP] Japan ............................ 60-218765

[51] Int. Cl.⁴ ........................................... A61C 13/00
[52] U.S. Cl. .................................................. 433/215
[58] Field of Search ............................ 433/215–219; 204/290, 20; 427/2

[56] References Cited

U.S. PATENT DOCUMENTS 3,997,637 12/1976 Rogers ........................... 204/20 X
4,125,442 11/1978 Rogers ........................... 427/405 X
4,247,575 1/1981 O'Connell et al. ................. 427/2
4,295,951 10/1981 Bommoraju et al. ......... 204/290 F X

FOREIGN PATENT DOCUMENTS 203748 4/1982 Japan .
69010 9/1983 Japan .
69177 9/1983 Japan .

OTHER PUBLICATIONS

The Journal of the Japan Prosthodontic Society, vol. 28, pp. 1023–1033 (1984), Adhesive Strength of Adhesive Resin Atsushi Yamashita, et al.

*Primary Examiner*—Nancy A. B. Swisher
*Attorney, Agent, or Firm*—Oblon, Fisher, Spivak, McClelland & Maier

[57] ABSTRACT

A restorative dental material is disclosed which comprises a metal casting with an electroplated tin coat containing polymer particles being formed thereon. Such restorative material can be obtained by electroplating the bonding surface of the metal casting using a plating bath containing Sn++ with polymer particles dispersed therein. An adhesive containing an acid group-containing polymerizable monomer as an adhesive component is applied to the bonding surface having the tin plating layer containing polymer particles and the material is firmly fixed to one or more teeth or other prosthetic appliances.

5 Claims, No Drawings

RESTORATIVE DENTAL MATERIAL AND METHOD OF RESTORING TEETH USING SAME

FIELD OF ART

This invention relates to a restorative dental material comprising a metal casting with an improved bonding surface, which material is to be fixedly adhered to one or more teeth or one or more other prosthetic appliances made of a variety of materials (noble metals, base metals, ceramics, organic macromolecular materials, etc.) in restorative dental treatment.

BACKGROUND ART

Today, metal castings such as inlays, crowns and bridges are in wide use in prosthetic restoration in dentistry. In dental treatment, such metal castings need to be fixed to teeth or other prosthetic appliances made of various materials and therefore a number of fixation methods therefor have been investigated. In particular, as a result of recent development of adhesive resins capable of adhering satisfactorily to teeth as well as to metals, the technique of effecting fixation using adhesives has attracted attention.

In the technology of adhesion fixation, the surface treatment of metal castings is important and is a decisive factor for the functional period of prosthetic appliances. Previously, the present inventors reported that provision of an electroplated tin coat on metal castings, which is to be followed by application of an adhesive onto the tin coat, is effective as such surface treatment (The Journal of the Japan Prosthodontic Society, volume 28, pages 1023-1033, 1984). However, further investigation has shown that said treatment is till unsatisfactory in respect to bond strength and long-term water resistance and, therefore, improvements are desired.

DISCLOSURE OF THE INVENTION

Accordingly, an object of the present invention is to improve the bond strength and durability of the adhesion bond between metal castings and teeth or prosthetic appliances made of various materials so that said bond can be maintained for a prolonged period of time.

Such object of the invention can be accomplished by providing a restorative dental material which is a metal casting with a plated tin coat layer containing polymer particles being formed on the bonding surface of said metal casting. Such restorative dental material can be produced by electroplating the bonding surface of a metal casting using an $Sn^{++}$-containing plating solution or bath with polymer particles dispersed therein. To the bonding surface having such polymer-containing tin plating, there is applied an adhesive composition containing, as an adhesive component, a polymerizable monomer having an acid group, and the metal casting is then firmly fixed to a tooth or teeth or some other prosthetic appliance or appliances.

BEST MODE FOR CARRYING OUT THE INVENTION

In accordance with the invention, the metal casting includes all metal castings that are casting products for dental treatment purposes, are variegated in form and shape and are to be held in position in the oral cavity of patients, more specifically inlays, onlays, crowns, bridges, clasps, splints, abutments and so forth. The metals which constitute such metal castings are, for example, noble metals such as gold, silver, platinum and palladium, precious alloys based on these noble metals (for instance, gold-based alloys, gold-palladium-silver alloys, silver-based alloys, etc.), base material such as nickel, chromium and cobalt, and nonprecious alloys based on these base metals (for example, nickel-chromium alloys, cobalt-chromium alloys, etc.). Prior to electroplating, these metal castings are desirably cleaned to a sufficient extent so that investments, dirt from the hands and other contaminants can be removed, since, without cleaning, there is the possibility of plated coat layer separation. For the purpose of cleaning, there may be used brushing, sandblasting, buffing, pickling, ultrasonic cleaning, electropolishing and electrolytic cleaning, among others. The bonding surface of the metal castings which is to be subjected to electroplating is desirably sandblasted using an abrasive about 10-100 μm in particle size because the resulting uneven surface remains uneven even after electroplated coat formation and this is advantageous from the bonding strength viewpoint.

A characteristic feature of the invention consists in that an electroplated tin coat layer containing polymer particles is formed on the bonding surface of the above-mentioned metal castings. For such plated coat layer formation, it is necessary to subject the metal castings to electroplating treatment in a tin plating bath with polymer particles added thereto. The plating bath to be used in the practice of the invention contains, as the main component, a stannous salt, such as stannous sulfate or stannous phenolsulfonate, namely $Sn^{++}$. Some examples of the plating bath composition usable in tin plating are given in "Hyomen Gijutsu Soran-Mekki Yokyoku Sanka Hen (Manual of Surface Technology, Plating and Anodic Oxidation Sections)", pages 357-363 (published on June 15, 1983 by Koshinsha), which see.

The polymer to be used in producing restorative dental materials according to the invention includes, among others, homopolymers and copolymers based on such monomers as vinyl chloride, styrene, ethylene, propylene, (meth)acrylate, vinyl acetate and butadiene. Preferred among such polymers are those polymers in which vinyl chloride or a (meth)acrylate accounts for at least 50 weight percent thereof. Polyvinyl chloride and poly(meth)acrylates are generally used, while such copolymers as vinyl chloride-vinyl acetate copolymer, vinyl chloride-(meth)acrylate copolymers, vinyl chloride-styrene copolymer and (meth)acrylate-styrene copolymers may also be used. Among these polymers, polymers containing vinyl chloride as the main component, in particular polyvinyl chloride, give high bonding strength. The (meth)acrylate monomer includes, among others, methyl (meth)acrylate, butyl (meth)acrylate, ethylene glycol di(meth)acrylate, tetraethylene glycol di(meth)acrylate, glycerol di(meth)acrylate, 2,2-bis[p-(γ-methaoryloxy-β-hydroxypropoxy)phenyl]propane (Bis-GMA), neopentyl glycol di(meth)acrylate, 2,2-bis(4'-methacryloxyethoxyphenyl)propane, trimethylolpropane tri(meth)acrylate and urethane (meth)acrylate, and either these monomers are used alone or two or more of them are used in combination. In practicing the invention, it is preferable that these polymers are composed substantially of particles not greater than 2.0 μm in particle size. When composed of particles greater in particle size, the polymers show a tendency toward poor electrodeposition of the polymer particles in the electroplated tin coat. It is more preferable that at least 80 weight percent of the total polymer quantity consists of particles not greater than 1.5 μm in particle size. It is preferable that a great number of polymer particles are uniformly dispersed in the electroplated tin coat deposited on the metal casting surface and, therefore, it is desirable that polymer particles small in particle size are dispersed in the plating bath so that such electrodeposited coat can be formed. These polymers are required to be dispersed in the plating bath in an amount of 0.5-25 weight percent based on the whole plating bath. When the polymer quantity is less than 0.5 weight percent, the effect of improving the adhesiveness of the metal casting surface is small whereas when the polymer quantity is greater than 25 weight percent, the bond strength-improving effect can hardly be produced because the polymer particles form a multilayer on the electroplated tin coat and the multilayer covers said tin coat. The shape of the particles to be used in accordance with the invention is generally spherical although it is not critical. Such polymer particles can be obtained by the conventional emulsion or suspension polymerization technique.

For obtaining restorative dental materials according to the invention, it is desirable to subject the above-mentioned polymers, before addition thereof to the plating solution, to surface treatment with a cationic surfactant of the general formula $R^1N^+(R^2)_3X^-$ wherein $R^1$ is an alkyl group containing 9-30 carbon atoms, $R^2$ is a hydrocarbon group containing 1-7 carbon atoms and X is a halogen. If electroplating is conducted using a plating bath with polymer particles dispersed therein as they are without such surface treatment or a plating bath with polymer particles dispersed therein after surface treatment with an anionic surfactant or a nonionic surfactant, it is difficult to make the electroplated tin coat formed on the metal casting surface contain an effective amount of the polymer particles. Therefore, the surface treatment with the above-mentioned cationic surfactant is very important. Typical examples of the cationic surfactant represented by the above general formula are stearyltrimethylammonium chloride, stearyltrimethylammonium bromide, cetyldimethylbenzylammonium bromide, nonyltriethylammonium chloride, triacontyltrimethylammonium chloride and hexadecylpyridinium chloride, among others. When other cationic surfactants than those having the above general formula, for example laurylamine acetate, polyoxyethylenealkylamines and so on, are used, the bonding strength-improving effect becomes decreased although the electroplated tin coat on the metal surface can contain polymer particles. Accordingly, it is desirable to use, in the production of restorataive dental materials in accordance with the invention, those cationic surfactants which are represented by the above general formula. The surface treatment of polymer particles with such a cationic surfactant is effected by immersing the polymer particles in a solution (e.g. alcohol solution) of the cationic surfactant, followed by taking out and solvent removal. The polymer particles surface-treated in the above manner are added to the plating solution and the solution is ready for electroplating of metal castings. For the electroplating, the plating solution with the polymer particles added thereto is placed in a dental electroplater (Kura Ace ®; produced by Nippon Avionics Co., Ltd.) for electroplating tin on metal castings, which has so far been on the market. In the practice of the invention, it is preferable that only the bonding surface part of the castings is plated. Therefore, the electroplating should desirably be carried out under conditions such that that metal casting surface which need not be plated is covered with a masking material. The plating layer thickness is desirably within the range of 0.02-10 μm. Generally, it is 0.1-2 μm. The number of polymer particles in the plating layer depends on the polymer concentration in the plating bath. Generally, however, said number is within the range of $10^4$-$10^7$ per square millimeter of plated surface area.

To the restorative dental material according to the invention which is made of a metal casting with a polymer particle-containing plated tin coat formed on the bonding surface thereof in the above manner, there is then applied an adhesive and one or more teeth or other prosthetic appliances (made of porcelains, cured composite resins, base metal castings, other tin-plated noble metal castings, etc.) are fixed to said bonding surface. The adhesive to be applied to the bonding surface of the restorative dental material according to the invention is preferably an adhesive containing a recently developed polymerizable monomer having an acid group $$\left[-COOH, \begin{matrix} O \\ \parallel \\ -P-OH, \\ | \\ OH \end{matrix} \begin{matrix} O \\ \parallel \\ -P-OH, \\ | \end{matrix} \begin{matrix} O \\ \parallel \\ -P-O-P-, \\ | \quad | \\ OH \quad OH \end{matrix} \begin{matrix} O \quad O \\ \parallel \quad \parallel \\ -P-O-P-, \\ | \quad | \\ OH \quad OH \end{matrix} \right.$$

$$\left. \begin{matrix} O \quad O \\ \parallel \quad \parallel \\ -C-O-C-, \end{matrix} \begin{matrix} O \\ \parallel \\ -P-X, \\ | \\ X \end{matrix} \begin{matrix} O \\ \parallel \\ -P-X, \\ | \end{matrix} \begin{matrix} O \\ \parallel \\ -C-X \end{matrix} \right.$$

(X being halogen), etc.]. Typical examples of such acid group-containing monomer and the details of the adhesive composition are disclosed in JP (Kokai) No. 52-113089, JP (Kokai) No. 58-21607, JP (Kokai) No. 54-11149, JP (Kokai) No. 57-151607, U.S. Pat. No. 4,182,035, U.S. Pat. No. 4,259.075, U.S. Pat. No. 4,539,382, GB No. 2000789, EP No. 0058483 and so on, where such acid group-containing monomer as mentioned above is generally a (meth)acrylate monomer such as given below:

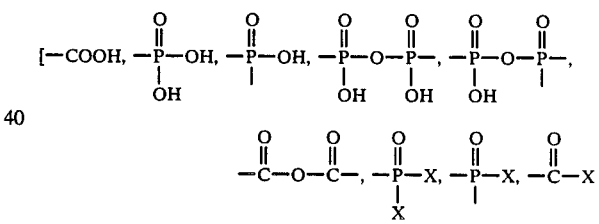

(n being an integer of 2-40)

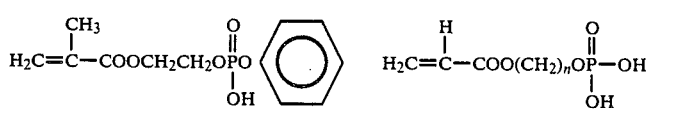

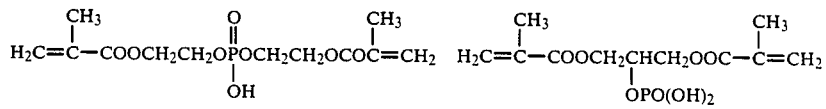

-continued

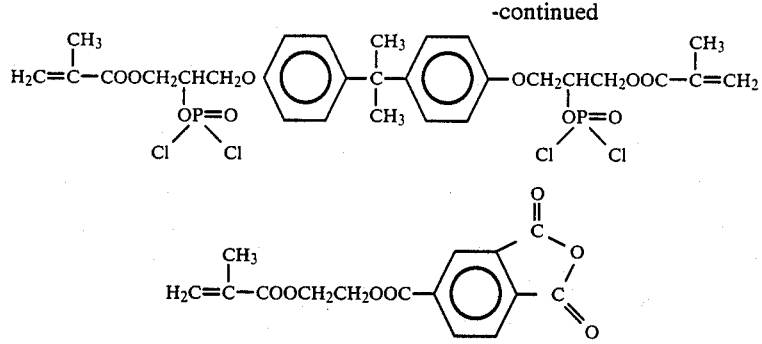

The adhesive composition is prepared by adding a copolymerizable (meth)acrylate monomer [ethylene glycol di(meth)acrylate, neopentyl glycol di(meth)acrylate, Bis-GMA, etc.] as a diluent to said acid group-containing monomer and further adding an initiator and, as necessary, a filler and so forth. The composition is applied to the restorative dental material according to the invention. And, as mentioned above, one or more teeth or other prosthetic appliances are further laid on said material and the adhesive is cured to complete the restorative dental treatment.

INDUSTRIAL APPLICABILITY

The restorative dental material according to the invention which comprises a metal casting with a plated tin coat containing polymer particles being formed on the bonding surface thereof can be fixedly and firmly bonded to one or more teeth or other prosthetic appliances. Therefore, the material can function for a prolonged period of time without separation of the casting or other troubles. Accordingly the restorative dental material according to the invention is very effective in dental treatment.

EXAMPLE 1

Two polymers, namely polymethyl methacrylate (hereinafter abbreviated as "PolyMMA") and poly-2,2-bis(4'-methacryloxyethoxyphenyl)propane (hereinafter abbreviated as "PolyBMEPP"), were prepared and respectively added to a tin plating solution. Using each plating solution, a plated tin coat containing polymer particles was formed on the surface of a gold alloy casting. The experiment conditions are given below in detail.

(i) Polymer preparation (1) PolyMMA: Methyl methacrylate was emulsion polymerized referring to the method of Takagi et al. [Kobunshi Gosei no Jikken Hoho (Experimental Methods in Macromolecular Synthesis), pages 149-150, published 1972 by Kagaku Dojin]. After polymerization, the polymer was washed with water and dried. Thus was prepared a polymer powder composed of spherical particles 0.1-0.2 μm in size.

(2) PolyBMEPP: 2,2-Bis(4'-methacryloxyethoxyphenyl)propane was suspension polymerized in accordance with the method of Suzuki et al. (The Journal of the Japanese Society for Dental Materials and Devices, vol. 2, No. 5, pages 564-570, 1983). There was obtained a polymer powder composed of spherical particles 0.3-2.0 μm in size.

(3) Surface treatment of the polymers obtained: Two grams (2 g) of each polymer obtained in the above manner was suspended in a solution of 9.2 g of stearyltrimethylammonium chloride (Kotamin ®; Kao Co., Ltd.) in 21.6 g of n-propyl alcohol, the suspension was stirred for 2.5 hours and the polymer was then collected by suction filtration.

(ii) Preparation of polymer-containing plating solutions

The polymer powders surface-treated in (i) were respectively added to a stannous sulfate-containing plating solution (Sn-100; Nippon Avionics Co., Ltd.) to a concentration of 5 weight percent.

(iii) Preparation of noble metal test pieces

Noble metal test pieces were prepared by soldering a Type IV gold alloy disk (Shofu Inc.), 7 mm in diameter and 2 mm in thickness, to an SUS 304 stainless steel body, followed by polishing with a #600 emery paper until the noble metal surface for bonding occurred as a plane perpendicular to the longer axis.

(iv) Electroplating

The above polymer-containing plating solutions were respectively placed in a tin electroplater (Kura Ace ®; Nippon Avionics Co., Ltd.) and the noble metal surface for bonding as described in (iii) was plated for 60 seconds under conditions of a voltage of 4 V and a current of 200 mA. For comparison, test pieces were prepared by conducting electroplating in the same manner using a stannous sulfate-containing plating solution with no polymer particles added thereto.

Observation of the noble metal surfaces obtained after the above electroplating treatment under a scanning electron microscope (magnification: ×10,000) gave the following findings:

When the electroplating was conducted in the polymer powder-free tin plating bath:

Polygonal tin crystal particles about 0.2-0.3 μm in size as electrodeposited uniformly on the noble metal surface were observed.

When the electroplating was conducted in the PolyMMA powder-containing tin plating bath:

In addition to and in admixture with polygonal tin crystal particles about 0.2-0.3 μm in size as uniformly deposited on the surface, spherical polymer particles seemed to be present and almost equal in size to tin crystals. However, the both kinds of crystals could hardly be distinguished one from the other due to close resemblance in size therebetween.

When the electroplating was conducted in the PolyBMEPP powder-containing tin plating bath:

Since, in particle size, the PolyBMEPP powder was 0.5-1.0 μm, hence greater than the PolyMMA, PolyBMEPP particles were easily distinguishable from tin crystals. There were observed polymer particles scattered in gaps among tin crystals on the noble metal surface.

As is evident from the above, the electroplating using the polymer powder-containing tin plating baths allowed formation of a polymer particle-containing plating layer on the noble metal surface.

In the next place, the noble metal test pieces electroplated in the above manner were subjected to adhesion testing for bonding strength measurement as follows:

(a) Adhesive

Two adhesives, namely Super-Bond C&B ® (Sun Medical Co., Ltd.; containing, as an adhesive component, 4-methacryloxyethyl trimellitate anhydride) and Panavia EX ® (Kuraray Co., Ltd.; containing, as an adhesive component, a phosphate monoester monomer), were used.

(b) Preparation of test pieces for adhesion testing

The above adhesives were respectively kneaded and heaped up on the surface of the electroplated noble metal test pieces, followed by butt jointing to cylindrical SUS 304 stainless steel rods blasted with 50 $\mu$m $Al_2O_3$.

(c) Bonding strength measurement

The test pieces for adhesion testing were immersed in water at 37° C. for 24 hours or at 70° C. for 30 days and then measured for bonding strength at a pulling rate of 2 mm/min using an Instron type universal testing machine (Shimadzu Corp. model DCS-2000 autograph).

The results of the bonding strength measurement as obtained for the case where Super-Bond C&B was applied to the Type IV gold alloy test pieces are shown in Table 1.

TABLE 1

| Electroplated layer | Bonding strength (kg/cm) (After immersion in water at 37° C. for 24 hours) |
|---|---|
| Tin layer (free of polymer particles) | 202 |
| Tin layer containing PolyMMA particles | 351 |
| Tin layer containing PolyBMEPP particles | 332 |

The above data indicate that the noble metal castings with a polymer particle-containing electroplated tin coat formed on the bonding surface thereof are obviously superior in adhesion properties.

The results of bonding strength measurement as obtained for the case where Panavia EX was applied to the Type IV gold alloy test pieces are shown in Table 2.

TABLE 2

| Electroplated layer | Bonding strength (kg/cm) | |
|---|---|---|
| | After immersion in water at 37° C. for 24 hours | After immersion in water at 70° C. for 30 days |
| Tin layer (free of polymer particles) | 304 | 296 |
| Tin layer containing PolyMMA particles | 449 | 413 |
| Tin layer containing PolyBMEPP particles | 472 | 511 |

The data in Table 2 clearly show that the noble metal castings provided with a polymer particle-containing electroplated tin coat on the bonding surface are obviously superior in adhesion properties. Furthermore, it is surprising that they can hold the high adhesion strength for a prolonged period of time.

EXAMPLE 2

(1) Preparation of polymer particles

Two polymers, namely PolyBMEPP and polyvinyl chloride (hereinafter abbreviated as "PolyVC"), were used. The PolyBMEPP used was a fraction of polymer particles 0.5–1.0 $\mu$m in size as obtained by sieving spherical polymer particles produced by suspension polymerizing 2,2-bis(4'-methacryloxyethoxyphenyl)propane in the same manner as described in Example 1. The PolyVC used was Mitsubishi-Monsanto's Oparon 440 ® (the average particle size being 1.0 $\mu$m; particles not more than 1.5 $\mu$m in size accounting for not less than 80 weight percent). This was used as it was without sieving.

Each polymer was suspended in a solution of stearyltrimethylammonium chloride (cationic surfactant) in n-propyl alcohol (the stearyltrimethylammonium chloride concentration being 30 weight percent) and, after 2.5 hours of stirring, the surface-treated polymer was recovered by suction filtration.

For comparison, the above procedure was followed using a 30 weight percent aqueous solution of sodium lauryl sulfate (anionic surfactant) or a 30 weight percent solution of Tween 80 ® (Kao Co., Ltd.; nonionic surfactant) in n-propyl alcohol in lieu of the above-mentioned) stearyltrimethylammonium chloride solution in n-propyl alcohol to give sodium lauryl sulfate- or Tween 80-treated polymer particles.

(2) Preparation of plating solutions with polymer particles dispersed therein

Plating solutions were prepared by dispersing the PolyBMEPP or PolyVC particles surface-treated with stearyltrimethylammonium chloride in a plating solution containing stannous sulfate as the main component, to a concentration within the range of 0.5–20 percent by weight on the whole plating solution basis.

For comparison, plating solutions with PolyVC particles without surface treatment or PolyVC particles surface-treated with sodium lauryl sulfate or Tween 80 (Kao Co., Ltd.) dispersed therein were also prepared.

(3) Preparation of metal test pieces

Metal test pieces were prepared by soldering a Type IV gold alloy disk (Shofu Inc.), 7 mm in diameter and 2 mm in thickness, to an SUS 304 stainless steel body, followed by polishing with a #600 emery paper until the metal surface for bonding formed a plane perpendicular to the major axis. Furthermore, a Ni-Cr alloy (SB-Bondloy ®; Towa Giken Co., Ltd.), and a gold-palladium-silver alloy (Castwell ®; G-C Dental Industrial Corp.) were also treated in the same manner as above to give further test pieces.

(4) Electroplating

Each plating solution obtained in the above manner (a solution containing stannous sulfate as the main component with the PolyBMEPP or PolyVC particles treated with stearyltrimethylammonium chloride being dispersed therein) was placed in a tin electroplater (trademark: Kura Ace; Nippon Avionics Co., Ltd.) and electroplating was performed on the above-mentioned metal surface for bonding for 100 seconds under conditions of a voltage of 4.5 V and a current of 75 mA. For comparison, electroplating was attempted following the above procedure and using a stannous sulfate-containing plating solution without addition of polymer particles or using a stannous sulfate-containing plating solution with sodium lauryl sulfate- or Tween 80-treated polymer particles dispersed therein.

(5) Results of electroplating (i) Observation of electroplated bonding surfaces

When the bonding surface of each of the Type IV gold alloy test pieces as electroplated in the plating bath containing 5 weight percent of the surface treatment-free PolyVC or the sodium lauryl sulfate- or Tween 80-treated PolyVC was observed under a scanning electron microscope (magnification: ×10,000), only a crystalline Sn coat free of polymer particles was found on the gold alloy surface for bonding in each case.

On the contrary, polymer particles were found on the gold alloy surface for bonding in any of the cases where the electroplating was performed in the plating bath containing 1, 5 or 15 weight percent of stearyltrimethylammonium chloride-treated PolyVC. It was noted that the quantity of the polymer deposited on the bonding surface increased with the increasing polymer concentration in the plating bath. When the concentration was 15 weight percent, the whole metal surface for bonding was covered with polymer particles.

As is clear from the above findings, the treatment of polymer particles with the cationic surfactant stearyltrimethylammonium chloride was confirmed to be effective in the formation, on the bonding surface, of an electroplated layer containing polymer particles.

(ii) Bonding strength measurement

The metal test pieces electroplated in the plating baths containing 0.5-20 weight percent of the stearyltrimethylammonium chloride-treated PolyBMEPP or PolyVC or in a plating solution free of such polymer were subjected to adhesion testing for bonding strength measurement in the following manner.

(a) Adhesive

Panavia EX® (Kuraray Co., Ltd.; containing a phosphate monoester monomer as an adhesive component) was used.

(b) Preparation of test pieces for adhesion testing

The above adhesive was kneaded and heaped up on the surface of each electroplated metal test piece, followed by butt adhesion to a cylindrical SUS 304 stainless steel rod blasted with 50 μm Al$_2$O$_3$ and anodized for 30 seconds in an EZ-Oxisor® anodizer (Towa Giken) at 3 V and 5 A.

(c) Bonding strength measurement

The test pieces for adhesion testing were immersed in water at 37° C. for 24 hours and then measured for bonding strength at a pulling rate of 2 mm/min on an Instron type universal tester (Shimadzu model DCS 2000 autograph).

(d) Results of measurement

When the Type IV gold alloy was electroplated:

The results obtained by performing the adhesion test using the Sn-electroplated Type IV gold alloy test pieces are shown in Table 3.

TABLE 3

| Plating solution used for treating gold alloy test pieces | | Bonding strength (kg/cm$^2$) |
|---|---|---|
| Kind of polymer | Concentration (wt %) | |
| Polymer-free | | 246 |
| PolyBMEPP | 1 | 351 |
| | 5 | 472 |
| | 10 | 507 |
| | 15 | 413 |
| PolyVC | 0.5 | 354 |
| | 1 | 385 |
| | 5 | 678 |
| | 10 | 484 |
| | 15 | 412 |
| | 20 | 348 |

The above results indicate that when an electroplated tin coat containing polymer particles has been formed on the bonding surface, the adhesive can firmly adhere to the Type IV gold alloy surface. Even when the polymer concentration in the plating solution is as low as 0.5 weight percent, the bonding strength increasing effect is remarkable and, for PolyVC, the strength value is maximum at a polymer concentration of 5 weight percent and, for PolyBMEPP, at a concentration of 10 weight percent. At these concentrations, the numbers of polymer particles deposited were $4 \times 10^5$ and $6 \times 10^5$ per square millimeter of electroplated surface, respectively. The reason why such high bonding strength can be achieved is supposedly that, as compared with the case where Sn alone is electroplated, the wettability to the adhesive is improved as a result of polymer electrodeposition on the metal surface for bonding. In particular, it is a quite unexpected finding that the presence of PolyVC in the tin coat layer led to much higher bonding strength as compared with PolyBMEPP.

When the Ni-Cr alloy and gold-palladium-silver alloy were electroplated:

The adhesion test performed with the electroplated Ni-Cr alloy and gold-palladium-silver alloy test pieces gave the results shown in Table 4.

TABLE 4

| | Plating solution | | |
|---|---|---|---|
| Kind of metal | Polymer | Concentration (wt %) | Bonding strength (kg/cm$^2$) |
| Ni—Cr alloy | Polymer-free | | 229 |
| (SB—Bondloy) | PolyVC | 5 | 434 |
| Gold-palladium- | Polymer-free | | 222 |
| silver alloy (Castwell) | PolyVC | 5 | 415 |

The data given in Table 2 clearly indicate that, also for the Ni-Cr alloy and gold-palladium-silver alloy, the formation of the electroplated tin coat layer containing polymer particles is effective in increasing the bonding strength.

EXAMPLE 3

For applying an adhesion bridge (bridge to be applied with an adhesive) made of Type IV gold alloy to a patient with right mandibular premolar defect, the bonding surface of said bridge was sandblasted with 50 μm alumina abrasive grains and then electroplated using the plating solution containing 5 percent of polyvinyl chloride particles (Oparon 440) as prepared in Example 2. An adhesive for dental use (Panavia EX) was applied to this surface and the bridge wings were fixedly adhered to the teeth on both sides of the missing tooth. The bonding area enamel of the teeth to which the brige was bonded had been treated in advance with a 40% aqueous phosphoric acid for 90 seconds. This enabled firm fixation of the bridge.

We claim:

1. A method of restoring teeth, which comprises:
   subjecting a bonding surface of a metal casting for dental use to electroplating in a plating bath containing stannous ions and polymer particles dispersed therein, so as to produce a tin layer which contains polymer particles therein on said metal casting,
   applying an adhesive containing a polymerizable monomer having an acid group to the tin layer electroplated on said metal casting to produce an adhesive-coated surface of said metal casting, and then
   bonding said adhesive-coated surface of said metal casting to a tooth or a prosthetic dental applicance.

2. The method of restoring teeth of claim 1, wherein said acid group is an acid group selected from the group consisting of

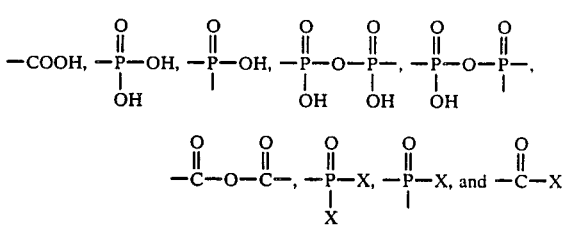

wherein X represents halogen.

3. The method of restoring teeth of claim 1, wherein said polymer particles are poly(meth)acrylate particles.

4. The method of restoring teeth of claim 1, wherein said polymer particles are polyvinyl chloride particles.

5. The method of restoring teeth of claim 1, wherein the metal constituting said metal casing is a noble metal or a noble metal-based alloy.

* * * * *